US00PP29880P3

(12) United States Plant Patent
Keithly

(10) Patent No.: US PP29,880 P3
(45) Date of Patent: Nov. 27, 2018

(54) ASIAN PEAR TREE NAMED 'PEGGY PEAR'

(50) Latin Name: *Pyrus pyrifolia*
Varietal Denomination: Peggy Pear

(71) Applicant: Stark Bro's Nurseries & Orchards Co., Louisiana, MO (US)

(72) Inventor: Doug Keithly, Yakima, WA (US)

(73) Assignee: Stark Bro's Nurseries & Orchards Co., Louisiana, MO (US)

( * ) Notice: Subject to any disclaimer, the term of this patent is extended or adjusted under 35 U.S.C. 154(b) by 559 days.

(21) Appl. No.: 14/121,198

(22) Filed: Aug. 11, 2014

(65) Prior Publication Data

US 2016/0044844 P1 Feb. 11, 2016

(51) Int. Cl.
*A01H 5/08* (2018.01)

(52) U.S. Cl.
USPC ..... Plt./178
CPC ..... *A01H 5/0881* (2013.01)

(58) Field of Classification Search
USPC ..... Plt./178
CPC ..... A01H 5/0881
See application file for complete search history.

(56) References Cited

U.S. PATENT DOCUMENTS

| | | | |
|---|---|---|---|
| PP6,075 | P | 1/1988 | Iwakiri |
| PP6,076 | P | 1/1988 | Iwakiri |
| PP6,726 | P | 4/1989 | Kanato |
| PP7,758 | P | 12/1991 | Machida |
| PP8,115 | P | 1/1993 | Kanato |
| PP9,179 | P | 6/1995 | Kotobuki |
| PP9,822 | P | 3/1997 | Spira |
| PP9,827 | P | 3/1997 | Spira |
| PP9,828 | P | 3/1997 | Spira |
| PP9,835 | P | 3/1997 | Spira |
| PP11,545 | P | 10/2000 | Kotobuki |
| PP11,656 | P | 11/2000 | Kotobuki |
| PP12,373 | P2 | 1/2002 | Machida |
| PP17,706 | P3 | 5/2007 | Doyle |
| PP18,876 | P3 | 6/2008 | Spira |
| PP18,976 | P3 | 6/2008 | Spira |

*Primary Examiner* — Kent L Bell
(74) *Attorney, Agent, or Firm* — Sandberg Phoenix & Von Gontard PC

(57) ABSTRACT

A new and distinct variety of Asian pear tree named 'Peggy Pear' characterized particularly by the globose to slightly turbinate shape of its fruit, its russet color at maturity, the thinner texture of the skin of the fruit of the 'Peggy Pear' compared to the skin of the fruit of its parent, the 'A-Ri-Rang', at maturity and its ripening at about September 20$^{th}$ in Yakima, Wash., which is about thirty (30) days earlier than the 'A-Ri-Rang' cultivar, and by the pear's hardiness, characterized in that it can be stored at 32° F. through the winter and maintain its quality until about May.

4 Drawing Sheets

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to a new and distinct variety of *Pyrus pyrifolia* an Asian pear tree, referred to by its cultivar name 'Peggy Pear'.

Discovery

The inventor has been growing Asian pears in Yakima, Wash. since 1989. He has grown four real cultivars: 'Hosui', 'A-Ri-Rang' (Korean Giant), 'Singo' and '20$^{th}$ Century' or 'Nijisseko'. He purchased the wood for his 'A-Ri-Rang' Asian Pear in the summer of 1989, and budded his trees shortly thereafter. The 'A-Ri-Rang' tree is a very large Korean cultivar that ripens very late, about November 5th or later in Yakima. In approximately 2008, the inventor found a naturally occurring limb mutation on one of his 'A-Ri-Rang' trees that had pears that were ripening much faster and had a different taste.

Propagation

A first act of asexual reproduction took place in Yakima, Wash. using buds from the above-referenced limb mutation. Additional trees were budded, creating a true sport limb of 'A-Ri-Rang'. The trees grew and yielded pears. The pears of the tree were also named 'Peggy Pear'. Thus both the tree and the fruit are referred to by that name. Furthermore, observations confirmed that my new cultivar represents a new and improved cultivar of Asian pear tree as particularly evidenced by early ripening and unique taste.

Uniqueness

The fruit, i.e., the pears from the disclosed tree, are not as large as its parent, the 'A-Ri-Rang' cultivar, but closer in size to a 'Hosui' (unpatented in the United States). The pear's shape is globose to slightly turbinate pome compared to most Asian pears, including the 'A-Ri-Rang', which is globose. The color of the skin of the fruit of the 'Peggy Pear' at maturity is russet, compared to the brown russetted color of the skin of the fruit of the 'A-Ri-Rang' at maturity. As to the texture of the skin of the fruit of the 'Peggy Pear' it is thinner compared to the skin of the fruit of the 'A-Ri-Rang' at maturity. The pear ripens about September 20$^{th}$ in Yakima, Wash., which is about thirty (30) days earlier than the 'A-Ri-Rang' cultivar. The pear can be stored at 32° F. through the winter and maintain its quality until about May.

Use

The tree and its fruit were observed for a period of time and is believed to be particularly useful anywhere that Asian Pear trees are raised; for example, in fruit trees orchards, field nurseries or in a landscape setting, and more particularly in these settings in the Pacific Northwest region of the United States.

Industry Representation

*Pyrus pyrifolia* are represented in the industry by a number of varieties and cultivars of *Pyrus pyrifolia.* In his Manual of Woody Landscape Plants, p. 811, Dr. Michael A. Dirr describes *Pyrus pyrifolia,* commonly named, "Chinese Sand Pear" variety. Also known are the following Asian pear trees: 'Shin Lin' (U.S. Plant Pat. No. 6,076); 'Daisui Li' (U.S. Plant Pat. No. 6,075); 'Asio 4' (U.S. Plant Pat. No. 9,822); 'Asio 2' (U.S. Plant Pat. No. 9,827); 'Asio 3' (U.S. Plant Pat. No. 9,828); 'Asio 1' (U.S. Plant Pat. No. 9,835); '85.10-23' (U.S. Plant Pat. No. 17,706); 'Asio 6' (U.S. Plant Pat. No. 18,876); and 'Asio 5' (U.S. Plant Pat. No. 18,976) and Japanese pear tree 'Syuugyoku' (U.S. Plant Pat. No. 6,726); Japanese pear tree 'Chikusui' (U.S. Plant Pat. No. 7,758); Japanese pear tree 'Yasato'; Japanese pear tree 'Hougetsu' (U.S. Plant Pat. No. 9,179); Japanese pear tree 'kotobui Shinsui' (U.S. Plant Pat. No. 11,545); Japanese pear tree 'Osa Gold' (U.S. Plant Pat. No. 11,656); and Japanese pear tree 'Akizuki' (U.S. Plant Pat. No. 12,373). Although this list is not exhaustive, it does represent what was generally available to the industry prior to 2008.

BRIEF SUMMARY OF THE VARIETY

The disclosed and claimed Asian pear tree is a new distinct variety of Asian pear tree which produces fruit that normally is ripe for harvesting and shipping on or about September 20$^{th}$ under the ecological and climatological conditions prevailing around Yakima, Wash. The fruit can be stored at about 32° F. and generally lasts through the winter and maintains its quality until about May.

The present cultivar produces medium to large sized globose to slightly turbinate pome. The fruit is typically green to golden yellow in color to russeted when ripe. The flesh of the fruit is firm and has a yellow to light golden hue when ripe.

BRIEF DESCRIPTION OF THE SEVERAL VIEWS OF THE DRAWINGS

The accompanying photographs depict the color of the tree and foliage of my new cultivar at approximately 5-6 years old as nearly as is reasonably possible to make the same in a color illustration of this character.

DESCRIPTION OF THE PREFERRED EMBODIMENT

Figure 1:
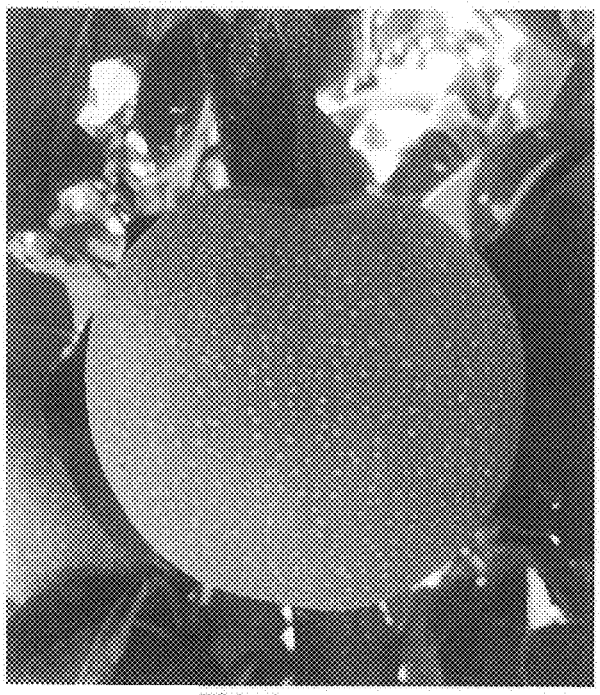
FIG. 1 is a photograph of a side view of the fruit of the new and distinct cultivar of Asian pear tree 'Peggy Pear'.
Figure 2:
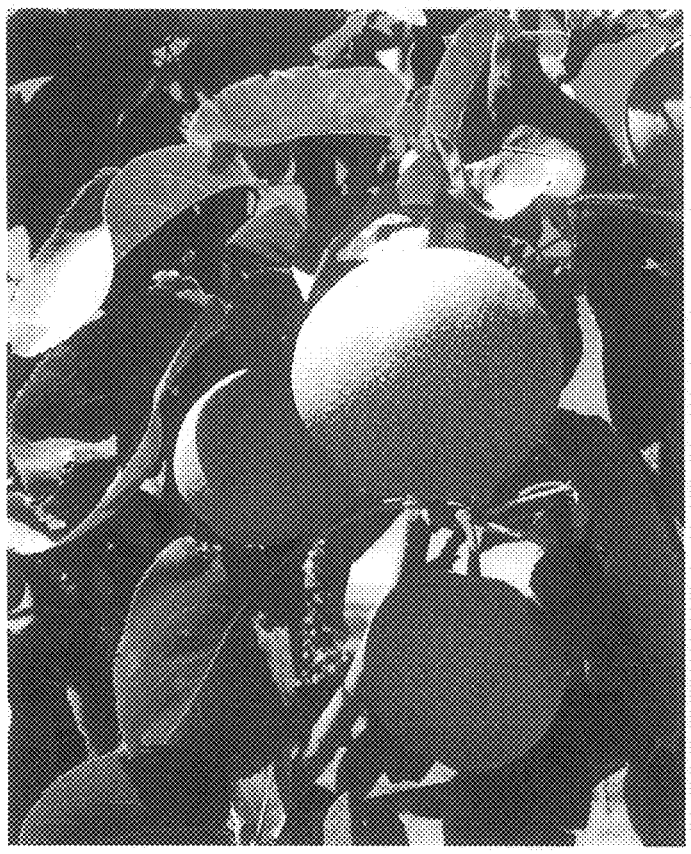
FIG. 2 is a photograph of the fruit of 'Peggy Pear' on the tree amid branches and leaves.
Figure 3:
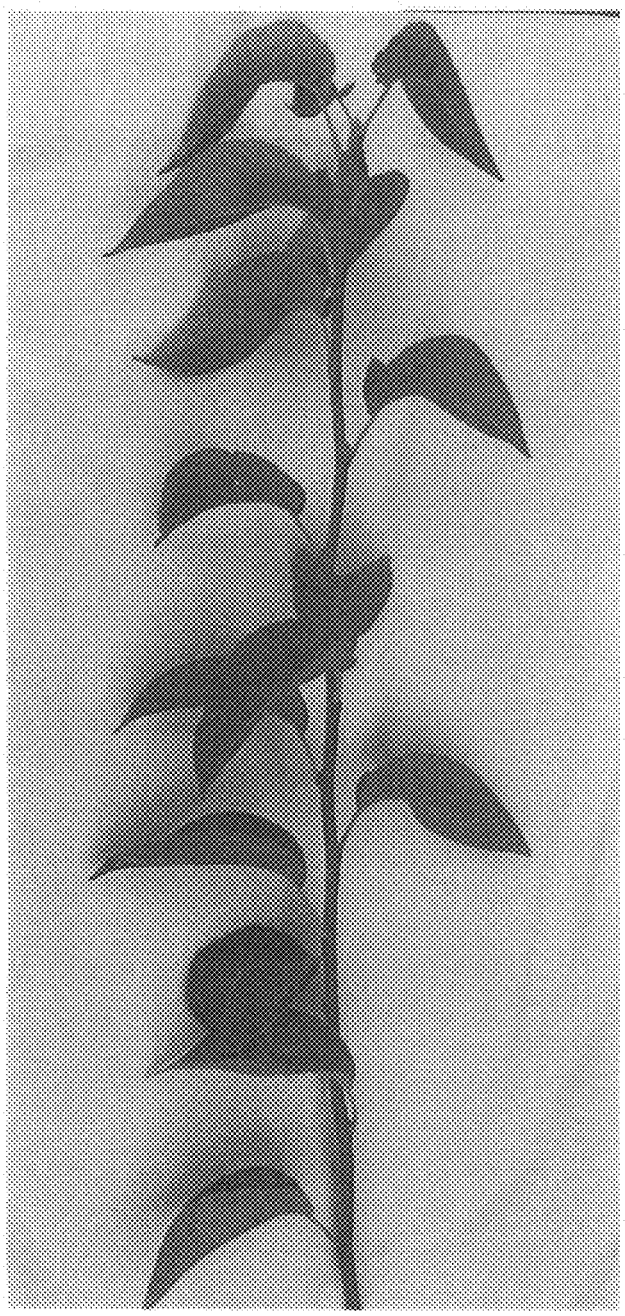
FIG. 3 is a photograph of a true sport limb of the new and distinct cultivar of Asian pear tree 'Peggy Pear'.
Figure 4:
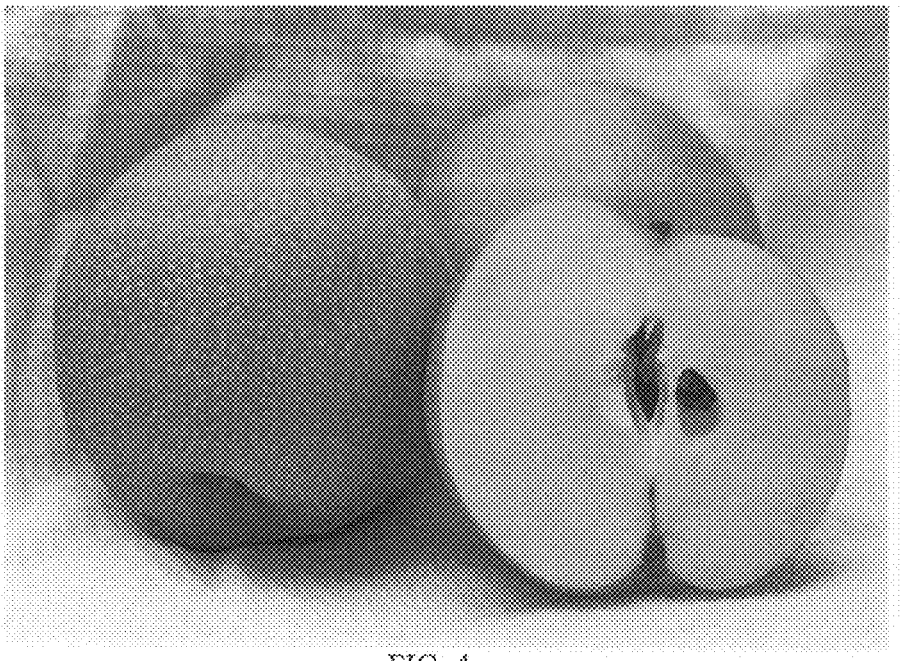
FIG. 4 is a photograph of a perspective view of a group of ripe fruit, with one of the fruit shown as a longitudinal section.

The following is a detailed description of my new cultivar of Asian Pear tree at approximately 5-6 years old with color terminology in accordance with The Royal Horticulture Society (R.H.S.) Colour Chart except where the context indicates a term having its ordinary dictionary meaning. My new tree has not been observed under all growing conditions and variations may occur as a result of different growing conditions. All progeny of my new variety of Asian Pear tree, insofar as have been observed, have been identical in all the characteristics described below.

Other than as set forth below, as of this time, no other characteristics of my new 'Peggy Pear' Asian pear tree have been observed by the inventor which are different from the characteristics common to Asian Pear trees.

Parentage: A true sport limb of 'A-Ri-Rang' first observed in 2008. Using buds from that limb mutation, additional trees were budded, creating a true sport limb of 'A-Ri-Rang'.

Locality where grown and observed: Yakima, Wash.

Tree:

*Size.*—Average for the species.

*Vigor.*—Vigorous and hardy under typical climatic conditions around Yakima, Wash.

*Tree form.*—Considered upright to upright spreading.

*Tree height.*—When measured at the end of the 2013 growing season, the present variety had a height to about 3.66 to about 4.27 meters. This growth included to about 1.22 to 1.40 meters of the current season's growth.

*Tree crown.*—Width — Approximately 1.5 meters. Trees of the present variety are growing in an orchard where spacing between the adjacent trees is about 1.83 meters, and the respective rows of trees are approximately 3.66 meters apart. The trees of the present variety are annually pruned into a narrow-upright vase training system.

*Productivity.*—Productive.

*Regularity of bearing.*—Regular.

*Trunk diameter.*—When measured at a distance of approximately 20 centimeters from the ground level the variety has a trunk diameter of approximately 11.4 centimeters.

Bark:

*Surface texture.*—Moderately cracked and roughened. However, some broad smooth areas are present.

*Bark color.*—Considered medium grey (Fan #4, Sheet 197-C).

*Bark lenticels.*—Numbers — Numerous and appearing roughened on their surfaces. Lenticels. — Shape — Considered oval.

*Lenticels.*—Size — Approximately 0.5 to about 1.0 millimeters in width, and from about 1.0 to about 3.0 millimeters in height.

*Lenticels.*—Color — Dark grey (Fan #4, Sheet 201-A).

Branches:

*Size.*—Considered normal in diameter for the species. The main scaffold branches of the observed tree range in diameter from about 6 to about 7.6 centimeters when measured at the base of the scaffold.

*Surface texture.*—Scaffold branches appear slightly smoother than the trunk surface, but have approximately the same grey color (Fan #4, Sheet 197-C).

*Lenticels.*—The lenticels seen on the branches appear to have the same development as that of the trunk, noted above.

*Upper branches.*—Size — The upper spreader branches range in size from about 5 to about 6.4 centimeters in diameter at their bases, while smaller hanger branches vary in thickness from about 0.79 to about 1.27 centimeters.

*Surface texture.*—Older branches — Two year old or older branches appear to have a netted surface texture, and further have numerous medium brown colored and calloused lenticels (Fan #4, Sheet 164-C).

*Older branches.*—Color — Grey-brown in color and nearly glabrous in surface texture (Fan #4, Sheet 201B).

*One year old shoots and spurs.*—Color — Considered brownish in color (Fan #4, Sheet 165-A) and having a moderately pubescent surface texture.

*Current season's shoots.*—Color — Dark brown (Fan #4, Sheet 177-A). These current season's shoots have a moderately pubescent surface texture.

*Actively growing shoots.*—Color — Light green (Fan #3, Sheet 138-A). Actively growing shoots have a highly pubescent surface texture of medium length. The pubescence appears wooly.

*Expanding shoot tips and young leaves.*—Color — Considered Orange-bronze in coloration (Fan #4, Sheet 172-C).

*Internode length.*—When measured on upright vigorous shoots, this ranges from about 4.45 to 5.08 centimeters between adjacent nodes. The length between the nodes as seen on smaller lateral shoots ranges from about 3.49 to about 3.81 centimeters.

Leaves:

*Size.*—Generally — Considered medium to large for the species. The measurements which follow have been taken from leaves growing near mid-shoot on vigorously growing current season's shoots.

*Leaf length.*—About 14.6 to about 15.24 centimeters including the leaf petiole.

*Leaf width.*—About 7.62 to about 8.255 centimeters.

*Leaf thickness.*—Considered normal for the species.

*Bud length and diameter.*—Typical and observed — Considered normal for this species.

*Surface texture.*—Young immature leaves are highly pubescent on both the upper and lower leaf surfaces. As these leaves mature however, much of this pubescence is lost.

*Mature leaf texture.*—Very slightly rugose. No glands are evident on the leaf.

*Leaf form.*—Generally — Considered variable from broadly lanceolate to ovate.

*Leaf base description.*—Typical and observed — Typical to slightly flared.

*Leaf apices.*—Shape — Acute and at times curled backward from the upper leaf surface. Most leaves appear somewhat folded upwards.

*Leaf surface.*—Texture — The leaf surfaces along the mid-vein are at times slightly wavy.

*Leaf color.*—Mature leaves — The upper leaf surface appears dark green (Fan #3, Sheet 137-A); and the lower surfaces are a lighter green in color (Fan #3, Sheet 138-B).

*Color.*—Mid-Vein — The primary mid-vein on the lower leaf surface is a pale yellow-green (Fan #3, Sheet 145-C).

*Leaf margins.*—Generally — Considered serrate and tipped with narrow, soft, sharp spines.

*Serrations.*—Size — Moderately small.

*Leaf margins.*—Shape — Slightly undulate.

*Leaf petiole.*—Size — Considered average and short, and further having a length of about 3.17 to about 3.81 centimeters, and a thickness of about 1.5 to 2.5 millimeters when measured at approximately mid-petiole.

*Petiole base.*—Shape — Typically considered wider and at times slightly flared, and having a thickness of about 1.5 to about 3.5 millimeters.

*Petiole.*—Color — Considered yellow-green on younger leaves (Fan #3, Sheet 144-D) and on older leaves (Fan #3, Sheet 145-C). Within the petiole groove and the petiole ridges, the color is increasingly darker (Fan #3, Sheet 138-B).

*Petiole.*—Surface texture — Lightly pubescent.

*Immature leaves.*—Surface texture — These leaves appear to have a higher degree of pubescence than mature leaves. No glands are present on the petiole.

*Leaf stipules.*—Generally — Small, thin, pale green stipules can typically be found on new growth. These leaf stipules are early deciduous.

*Leaf stipules.*—Form — Considered linearly lanceolate. The leaf stipules darken and deteriorate within increasing senescence.

Flowers:

*Flower buds.*—Size — Generally considered large, plump and conic in form. The buds are considered relatively free from the bearing stem and are considered hardy under Yakima, Wash. climatic conditions. The typical and observed average bud length and diameter are approximately 1.5 cm and 0.813 cm, respectively.

*Flower buds.*—Color — Reddish-brown (Fan #4, Sheet 175-A).

*Flower buds.*—Surface texture — Considered pubescent especially apically and over the interior side of the bud scales.

*Bloom time.*—Generally — Average to slightly early in relative comparison to other common Asian pear tree varieties growing at the same geographic location.

*Typical and observed bloom season.*—April 5-14 — Considered a normal range in Yakima, Wash., the location where observed.

*Date of full bloom.*—Observed at Yakima, Wash. on Apr. 14, 2012 and Apr. 5, 2013.

*Duration of bloom.*—The date and duration of bloom can be substantially effected by the amount of chilling hours that occur during a given year, and the geographical location where the variety is grown.

*Typical and observed flower height and diameter.*—Considered normal.

*Flower size.*—Generally — The typical and observed flower diameter when fully opened averages 5 to 5.5 cm.

*Bloom quantity.*—Considered abundant.

*Flowers per node.*—As many as 8 can be produced.

*Petal numbers.*—Typically 5, but extra petals can be observed. As many as 5 extra petals can sometimes be seen. Double petalled flowers (10 petals) can be found on many fruiting branches.

*Petal form.*—Considered variable, but most frequently appears ovate.

*Petal color.*—White (Fan #4, Sheet 155-D).

*Petal claw.*—Shape — Short and truncate in form.

*Petal margins.*—Shape — Undulate.

*Petal apices.*—Form — Variable and having a somewhat pointed tip.

*Flower pedicel.*—Size — These are variable from about 21 to about 30 millimeters in length, and from about 1.0 to about 1.5 millimeters in thickness.

*Flower pedicel.*—Color — Pale green (Fan #3, Sheet 145-C).

*Flower pedicel.*—Surface Texture — Pubescent, and further having moderately sparse filamentous pubescence.

*Floral nectaries.*—Color — Yellow-brown (Fan #3, Sheet 153-B). The floral nectaries become darker with increasing senescence.

*Calyx.*—Surface Texture — Slightly pubescent.

*Calyx.*—Color — Pale green (Fan #3, Sheet 145-B).

*Sepals.*—Surface Texture — Pubescent.

*Sepals.*—Size — Relatively small and broadly lanceolate in form.

*Sepals.*—Color — Green-yellow (Fan #3, Sheet 145-B).

*Anthers.*—Size — Considered average for the species.

*Anthers.*—Color — Considered a pale rose (Fan #1, Sheet 51-B). This color appears both ventrally and dorsally.

*Pollen production.*—Considered abundant in quantity.

*Pollen.*—Color — Yellow (Fan #1, Sheet 5-A).

*Stamens.*—Color — White (Fan #4, Sheet 155-D).

*Pistil.*—Form — The pistil of the present variety has five styles separated to the ovary.

*Pistil.*—Length — Somewhat variable from about 6 to 7 millimeters.

*Pistil.*—Surface Texture — Glabrous.

*Pistil.*—Color — Yellow-green (Fan #1, Sheet 1-D).

Fruit:

*Maturity when described.*—The fruit of the present cultivar of Asian pear tree 'Peggy Pear' is described at full commercial maturity hereinafter.

*Date of harvest.*—In 2013, the date of harvest was September 16. The date of harvest in 2012 was October 4. The date of harvesting is about thirty (30) days earlier than the 'A-Ri-Rang' variety. The date of harvest may be effected by seasonal variations. The date of harvesting, noted above, are those that were observed at Yakima, Wash.

*Fruit production.*—Per season per tree: when appropriately thinned, the typical and observed average amount of fruit produced per season per tree is about 200 to 250 lbs.

*Fruit size.*—Generally — Considered medium to large in size especially for the early date of maturity. For fruit harvested from well thinned trees, the fruit diameter was about 82.55 to about 88.9 millimeters; the fruit had a height of about 82.55 to about 88.9 millimeters, and an average typical and observed individual fruit weight of 9 to 12 oz.

*Fruit form.*—Generally — Slightly variable from nearly globose to slightly turbinate pome when viewed in its lateral aspect. The fruit is most frequently globose or very slightly oval when viewed in transverse section.

*Fruit symmetry.*—Somewhat variable, from fully symmetrical to slightly asymmetrical or considered lopsided.

*Fruit stem.*—Size — The fruit stem has a length dimension of about 34.98 to about 38.1 millimeters; and a thickness dimension of about 3.8 to about 4.7 millimeters.

*Fruit stem.*—Shape — Typically, considered slightly curved.

*Fruit stem.*—Color — Light green (Fan #3, Sheet 144-B).

*Fruit stem.*—Surface Texture — Moderately pubescent.

*Fruit lenticels.*—Color — Light tan and being slightly raised and oval in form on the fruit stem surface (Fan #4, Sheet 161-A).

*Stem cavity.*—Shape — Considered uniform and acute.

*Stem cavity.*—Size — Considered moderate. The width of the stem cavity ranges from about 23 to about 28 millimeters when measured across the shoulders of the fruit. The depth of the stem cavity is variable from about 6 to about 9 millimeters.

*Fruit basin.*—Shape — Globose in form; relatively wide; and of average depth. The fruit basin sides are sloping and have what appears to be a smooth surface. Some russetting is present within the basin where the sepals were attached to the fruit. The sepals are considered deciduous.

*Calyx.*—Form — The calyx opening is closed. Still further, the calyx tube is considered long and funnel shaped. Additionally, stamen remnants are often present in the calyx tube and are typically located in a marginal position.

*Core lines.*—Generally — These are distinct and clasping.

*Fruit core.*—Position — Distant and considered relatively far from the fruit stem.

*Fruit core.*—Size — 82.55 to about 88.9 millimeters.

*Fruit carpels.*—Generally — Five carpels are present and are located within the fruit core. The number of seeds per carpel (locule) and the average fruit carpel length and width is considered to be typical for this species.

*Fruit carpels.*—Shape — Obovate.

*Fruit carpel cells.*—Form — Generally speaking, these are closed in form although at times some open cells can be present.

*Fruit carpels.*—Surface Texture — The inner surface of the carpel wall is considered glabrous.

*Seeds.*—Numbers — Variable from 2 to as many as 10 per locule.

*Seeds.*—Size — Considered plump, and having a length of about 7.94 to about 9.53 millimeters; and a width from about 3.18 to about 4.76 millimeters.

*Seeds.*—(Typical and observed) — The shape of the seeds, both typical and observed, is considered to be normal for this species.

*Seeds.*—Thickness — About 3.18 millimeters.

*Seed apex.*—Form — Acute.

*Seed shape.*—Typical of this species.

*Seeds.*—Color — Dark Brown at full maturity (Fan #4, Sheet 175-A). The seeds color at full commercial maturity is a lighter tan-brown color (Fan #4, Sheet 164-B).

*Fruit skin.*—Thickness — Considered average.

*Fruit skin.*—Surface texture — Glabrous. The skin appears to tightly adhere to the underlying fruit flesh.

*Fruit skin.*—Flavor — Considered mild to neutral.

*Fruit skin.*—Color — Predominately yellow-green (Fan #3, Sheet 151-C), and occasionally, having light green lenticles (Fan #3, Sheet 1-D), which typically appears at an early stage of maturity. With advancing senescence, and at full commercial maturity, the fruit becomes a full substantially grayed-orange. or russet (Fan #4, Sheet 163-A) with light greyed-orange lenticles (Fan 4, sheet 163-C).

*Fruit skin.*—Lenticels — Present. These are small and relatively inconspicuous.

*Fruit skin lenticel color.*—Very pale yellow (Fan #1, Sheet 1-D).

*Bloom.*—Present, and considered very thin and transparent. The bloom extends substantially over the entire skin surface.

*Fruit flesh.*—Color — White with a very slight cream-yellow tint (Fan #1, Sheet 11-D).

*Fruit flesh.*—Texture — Crisp and considered very juicy.

*Stone cells.*—Generally — Present, and average in number. The stone cells are located in the vicinity of the core area.

*Ripening.*—Considered even. The fruit holds well on the tree.

*Fruit flavor.*—Considered sweet, refreshing and mild, with a brix typical of this species and having a very good commercial quality.

*Aroma.*—Considered pleasant, and slight.

*Resistance to insects and diseases.*—No particular susceptibility where noted. The present variety has not been intentionally tested to expose or detect any susceptibilities or resistance to any known plant and/or other fruit tree diseases.

The invention claimed is:

1. A new and distinct Asian Pear Tree named 'Peggy Pear' as illustrated and described herein.

* * * * *